United States Patent
Jung

(10) Patent No.: US 9,261,302 B2
(45) Date of Patent: Feb. 16, 2016

(54) IN-LINE INTERNAL PLUMBING LINE SANITIZER FOR APPLIANCES APPARATUS

(71) Applicant: Serina Solanda Jung, Orlando, FL (US)

(72) Inventor: Serina Solanda Jung, Orlando, FL (US)

(73) Assignee: Westmount, LLC, Orlando, FL (US)

( * ) Notice: Subject to any disclaimer, the term of this patent is extended or adjusted under 35 U.S.C. 154(b) by 125 days.

(21) Appl. No.: 14/288,644

(22) Filed: May 28, 2014

(65) Prior Publication Data
US 2015/0053276 A1    Feb. 26, 2015

Related U.S. Application Data

(60) Provisional application No. 61/959,306, filed on Aug. 20, 2013.

(51) Int. Cl.
| | |
|---|---|
| F25C 1/00 | (2006.01) |
| A61L 2/18 | (2006.01) |
| C02F 1/68 | (2006.01) |
| C02F 1/76 | (2006.01) |
| B01F 1/00 | (2006.01) |
| B67D 1/07 | (2006.01) |

(52) U.S. Cl.
CPC ... *F25C 1/00* (2013.01); *A61L 2/18* (2013.01); *B01F 1/0016* (2013.01); *C02F 1/688* (2013.01); *C02F 1/76* (2013.01); *B01F 2001/0055* (2013.01); *B01F 2001/0094* (2013.01); *B67D 1/07* (2013.01); *C02F 2303/04* (2013.01); *C02F 2307/10* (2013.01); *C02F 2307/14* (2013.01); *Y10T 137/0402* (2015.04); *Y10T 137/87676* (2015.04)

(58) Field of Classification Search
CPC .............. F25C 1/00; A61L 2/18; B67D 1/07; Y10T 137/0402; Y10T 137/87676; C02F 1/50; C02F 1/685; C02F 1/687; C02F 1/688; C02F 1/76; C02F 2103/02; C02F 2103/32; C02F 2303/04; C02F 2303/20; C02F 2307/10; C02F 2307/14
See application file for complete search history.

(56) References Cited

U.S. PATENT DOCUMENTS 3,772,193 A * 11/1973 Nelli ................... C02F 1/688
137/268

* cited by examiner

*Primary Examiner* — Lucas Stelling
(74) *Attorney, Agent, or Firm* — Antonio G. Tapia

(57) ABSTRACT

A new and useful in-line internal plumbing line sanitizers for appliances apparatus that sanitizes the internal plumbing lines of appliances such as refrigerators with integrated ice makers and drinking water dispensers, is easily adaptable, can be made in different sizes for use with various appliances, and can house a variety of sanitizing agents. The apparatus can also be used by an ordinary consumer, increases the safety and efficiency of internal plumbing line sanitation procedures, and eliminates the need for expensive replacement of internal appliance plumbing lines. This device is believed to be useful in the domestic and commercial settings. A device according to the invention is also believed to be favorable for use by appliance service technicians, as well as lay people who want to sanitize an appliance periodically.

15 Claims, 4 Drawing Sheets

IN-LINE INTERNAL PLUMBING LINE SANITIZER FOR APPLIANCES APPARATUS

CROSS-REFERENCE TO RELATED APPLICATIONS

This application claims the benefit of U.S. Provisional Application No. 61/959,306, filing date Aug. 20, 2014.

TECHNICAL FIELD

The present invention is in the technical field of line sanitizers. More particularly, the present invention is in the technical field of in-line fluid line sanitizers. More particularly, the present invention is in the technical field of in-line internal plumbing line sanitizers for appliances.

BACKGROUND OF THE INVENTION

In the current art, modern refrigerators often include the function of producing ice and dispensing drinking water. In order to accomplish these amenities, a home water line is required which carries water to the appliance and connects to the plumbing located on the back of the refrigerator, using a nut and ferrule. The water then travels into the appliance and goes to an ice maker and a water dispenser for use and consumption.

Over time, it is common for the water line to accumulate debris, rust, corrosion, mold, and other undesirable contaminants along the interior surfaces of the interior appliance plumbing lines. These contaminants may cause reduced function, accumulation of sedimentary and scale debris, impact taste, as well as potability and cause illness. Therefore these contaminants, which can include mineral scales, molds, and algae, are preferably flushed out of the water line using a cleaning and sanitizing means on a periodic maintenance schedule.

In order to address the problem of contaminated and dirty interior refrigerator water lines, some modern units possess an optionally replaceable water filter to remove sediment and other contaminants before use. This water filter usually is inserted by the user into the interior refrigerator compartment or along the base of the unit. This water filter however does not completely solve the problem of contaminated interior water lines. This is because the filter is too far downstream from the point of entry of the water at the back of the refrigerator. The water filter in the current art only cleanses the water in the final length of tubing to the ice maker and water dispenser. That length can in some instances be only a few inches long. In-line water filters in the current art do not clean, disinfect or condition the interior surfaces of the refrigerator water line between the point of entry of the home water line into the refrigerator and the optional water filter in modern units.

In the applicant's experience, there is a need for an in-line internal plumbing line sanitizers for appliances apparatus which: i) sanitizes internal plumbing lines of appliances such as refrigerators with integrated ice makers and drinking water dispensers, ii) is easily adaptable, iii) can be made in different sizes for use with various appliances, iv) can house a variety of sanitizing agents, v) can be used by an ordinary consumer, vi) increases safety and efficiency of internal plumbing line sanitation procedures, and vii) eliminates the need for expensive replacement of internal appliance plumbing lines. The device according to the present invention is believed to accomplish all of the foregoing objectives.

SUMMARY OF THE INVENTION

The present invention provides a new and useful in-line internal plumbing line sanitizer for appliances apparatus that sanitizes the internal plumbing lines of appliances such as refrigerators with integrated ice makers and drinking water dispensers, is easily adaptable, can be made in different sizes for use with various appliances, and can house a variety of sanitizing agents. The apparatus can also be used by an ordinary consumer, increases the safety and efficiency of internal plumbing line sanitation procedures, and eliminates the need for expensive replacement of internal appliance plumbing lines. This device is believed to be useful in domestic and commercial settings. A device according to the present invention is also believed to be favorable for use by appliance service technicians, as well as lay people who want to sanitize an appliance periodically.

The invention achieves its result of sanitizing internal appliance plumbing lines by using the existing volumetric flow rate of water from an existing water line to flush the system completely. The invention is used by attaching the apparatus between the water line in the environment, for example a water line in the kitchen in a home, and the appliance plumbing line, for example on the back of a refrigerator with ice machine and drinking water dispenser. When in use the water flows through the apparatus, thereby dissolving a sanitizing agent held within an interior chamber in the apparatus. The sanitizing agent mixes with the water and exits the apparatus in solution. Thereafter the sanitizing agent flows through the interior appliance plumbing lines and removes any contaminants, chemical, mineral or biological—returning the appliance to a clean state and improving the potability of the drinking water dispensed by the appliance. The user continues to flush water through the system until no indication of sanitizing agent is present, removes the apparatus, and finally reconnects the appliance to the water line to resume regular use.

Further features of the present invention will become apparent from the following detailed description and the accompanying drawings.

DETAILED DESCRIPTION OF THE INVENTION

As described above, the present invention provides a new and useful in-line internal plumbing line sanitizers for appliances apparatus that sanitizes the internal plumbing lines of appliances such as refrigerators with integrated ice makers and drinking water dispensers, is easily adaptable, can be made in different sizes for use with various appliances, and can house a variety of sanitizing agents. The apparatus can also be used by an ordinary consumer, increases the safety and efficiency of internal plumbing line sanitation procedures, and eliminates the need for expensive replacement of internal appliance plumbing lines. This device is believed to be useful in the domestic and commercial settings. A device according to the invention is also believed to be favorable for use by appliance service technicians, as well as lay people who want to sanitize an appliance periodically. The following description and accompanying drawings disclose at least one version of such a device.

Figure 1:
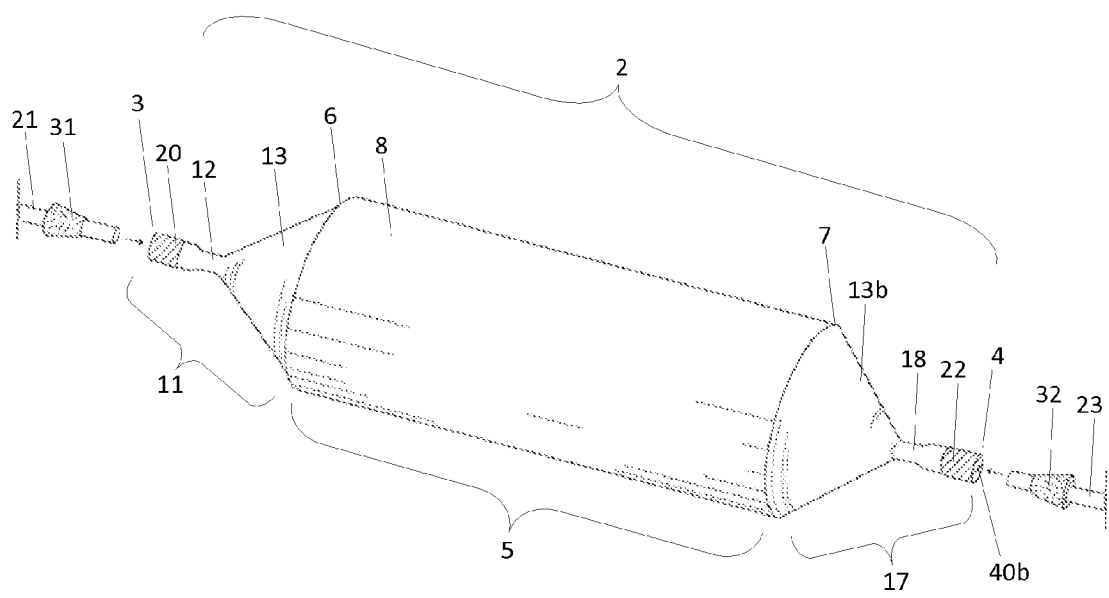
FIG. 1 is an external perspective view of an in-line internal plumbing line sanitizer for appliances apparatus according to the present invention.
Figure 2:
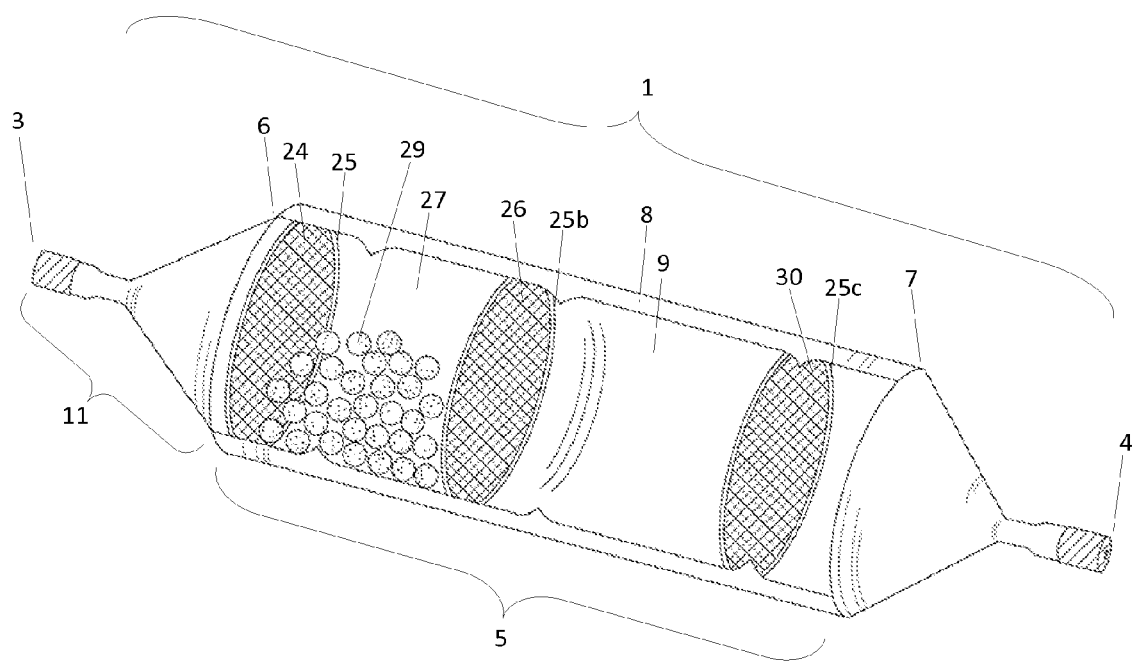
FIG. 2 is an internal perspective view showing the internal components of the apparatus.
Figure 3:
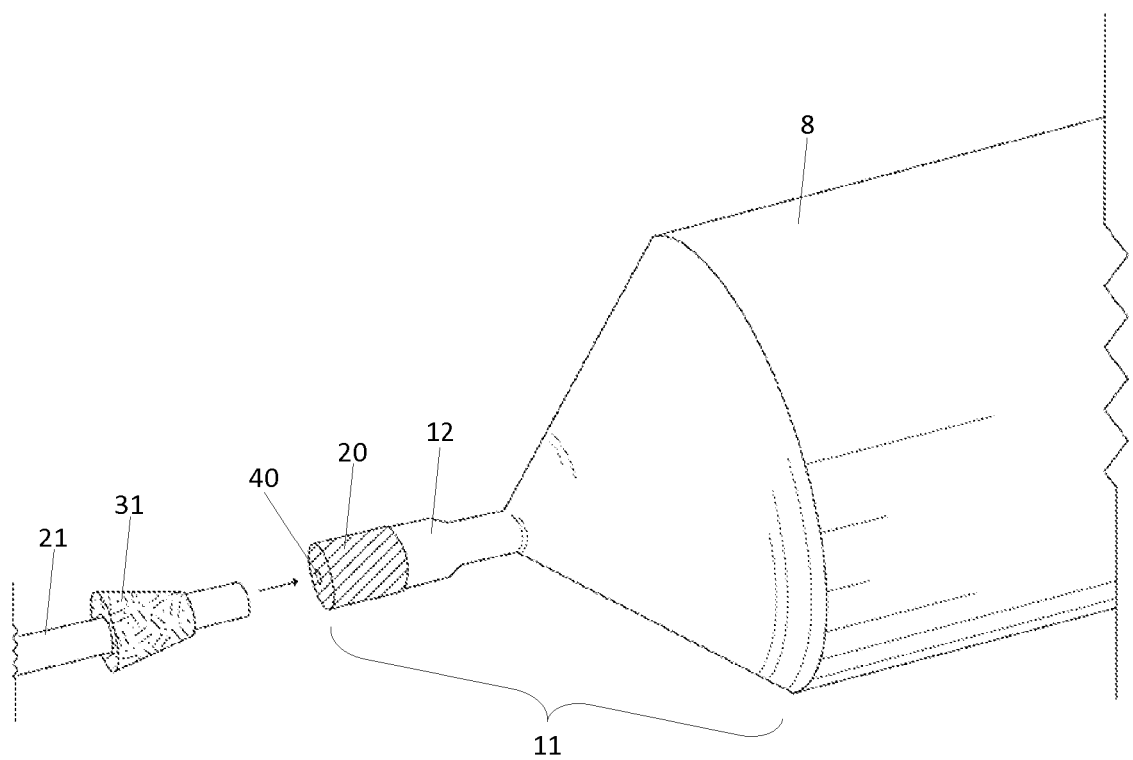
FIG. 3 is a detail view of the proximal end of the apparatus connected to a water line and in use.
Figure 4:
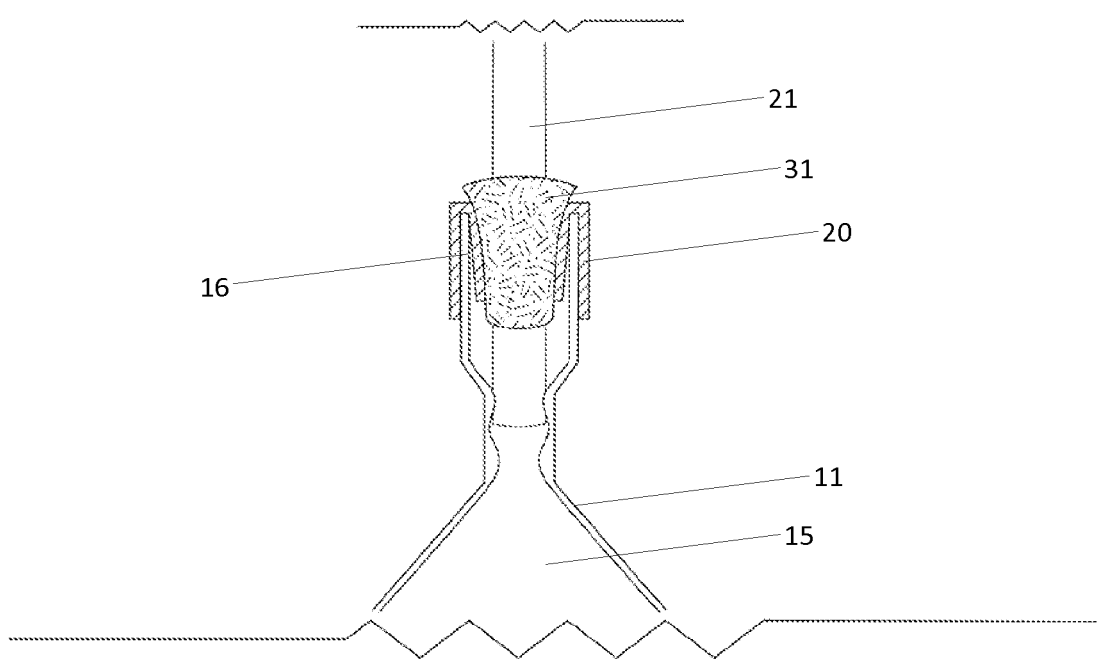
FIG. 4 is a detail cross section of the proximal end of the apparatus in use.

Referring now to the invention in more detail, in FIG. 1 to FIG. 4 there is shown a in-line internal plumbing line sanitizers for appliances apparatus 1 shown generally which comprises a cartridge 2 having a proximal end 3, a distal end 4 and formed by a rigid hull 5 which is substantially cylinder shaped and having a first end 6 and a second end 7, as well as an outer surface 8 and inner surface 9, thereby defining a cylindrical void 10 within. An in-flow end 11 is attached to the first end 6 of the hull 5. The in-flow end 6 has a substantially conical shape with and an in-flow nipple 12 extending from the in-flow end 6 of the apparatus 1. Together, the in-flow end 6 and the attached in-flow nipple 12 have an outer surface 13 and an inner surface 14, thereby defining a conical void 15 within. The in-flow nipple 12 also has a proximal opening 16 at the proximal end 3 of the apparatus 1.

An out-flow end 17 is attached to the second end 7 of the hull 5 and has a substantially conical shape with an out-flow nipple 18 extending from the out-flow end 17. Together, the out-flow end 17 and attached out-flow nipple 18 have a second outer surface 13b and a second inner surface 14b thereby defining a second conical void 15b within. The out-flow nipple 18 also has a distal opening 19 at the distal end 4 of the apparatus 1.

In more detail, still referring to the apparatus of FIG. 1 to FIG. 4, there is an in-flow boot 20, which is generally cylindrical, over and covering the proximal opening 16 of the in-flow nipple 12. The in-flow boot 20 is made from a flexible material such as rubber, and has a first pinhole aperture 40 located in the end of the in-flow boot 20 for receipt of an inserted water line 21 from the environment into the in-flow nipple 12 of the apparatus 1.

There is also an out-flow boot 22, which is generally cylindrical, over and covering the distal opening 19 of the out-flow nipple 18. The out-flow boot 22 is made from a flexible material such as rubber, and has a second pinhole aperture 40b located in the end of the out-flow boot 22 for receipt of an inserted appliance plumbing line 23 from the environment into the out-flow nipple 18 of the apparatus 1.

Together the out-flow boot 22 and in-flow boot 20 act to serve several purposes. Each act to seal and protect the interior contents of the apparatus during transport and prior to use. Further, each boot acts as an entry point into the apparatus 1 where the water line 21 enters the proximal opening 16 via the first pinhole aperture 40 and the appliance plumbing line 23 enters the distal opening 19 via the second pinhole aperture 40b of the device. Each pinhole expands as water line tubing enters the device. The in-flow boot 20 and out-flow boot 22 fold inward and form a primary seal between the apparatus and the water lines which is water tight and prevents back flow when the apparatus is in use.

Within the interior of the apparatus 1, a first sieve 24 which is generally planar and having a first circular perimeter 25 is located at the first end 6 and within the interior cylindrical void 10 of the hull 5. The first circular perimeter 25 of the first sieve is affixed and forms a tight seam with the hull 5. The first sieve 24 is a semi-permeable mesh having a plurality of perforations which allows the passage of fluid there through.

A second sieve 26 which is generally planar and having a second circular perimeter 25b is located between the first sieve 24 and the second end 7 of the hull 5 and within the interior cylindrical void 10 of the hull 5. The second circular perimeter 25b of the second sieve 26 is affixed and forms a tight seam with the hull 5. The second sieve 26 is a semi-permeable mesh having a plurality of perforations which allows the passage of fluid there through.

Further, there is a sanitizing agent holding chamber 27 in the interior cylindrical void 10 of the hull 5 near to the proximal end 3 of the apparatus 1 and is defined by the void created by nexus of the inner surface 9 of the hull 5, the first sieve 24 and second sieve 26.

There is also a mixing chamber 28 in the interior cylindrical void 10 of the hull 5 near to the distal end 4 of the apparatus 1 and is defined by the void created by the nexus of the inner surface 9 of the hull 5, the second sieve 26 and the out-flow end 17 of the apparatus 1.

A sanitizing agent 29 which is a plurality of water soluble crystals or beads, is located in the sanitizing agent holding chamber 27.

In an alternate embodiment of the apparatus, a third sieve 30 can also be present. The third sieve 30 is generally planar, has a third circular perimeter 25c and is located between the second sieve 26 and the second end 7 of the hull 5. The third circular perimeter 25c of the third sieve 30 is affixed and forms a tight seam with the hull 5. Further, the third sieve 30 is a semi-permeable mesh having a plurality of perforations which allows the passage of fluid there through.

In an alternate embodiment of the apparatus, a proximal end cap seal 31 is inserted onto the water line 21 in the environment. The proximal end cap seal 31 is a compressible material such as rubber, and creates a tight seal between the water line 21 and in-flow boot 20 when adjoined.

A distal end cap seal 32 can be inserted onto the appliance plumbing line 23 in the environment. The distal end cap seal 32 is a compressible material such as rubber, and creates a tight seal between the appliance plumbing line 23 and out-flow boot 22 when adjoined.

If present in an embodiment, the proximal end cap seal 31 and distal end cap seal 32 are pushed down into the proximal opening 16 and the distal opening 19 of the apparatus 1 and are utilized to create a tighter or redundant air tight and water tight seal when the apparatus is in use.

In at least one embodiment of the present invention, the sanitizing agent 29 is chlorine-based.

In an alternate embodiment of the present invention, the sanitizing agent 29 further comprises a water soluble dye that is visible when in solution. This water soluble dye acts as a visual indicator to the user that the sanitizing agent is still present and that she should continue to flush the system until no further dye is visibly emanating from the appliance.

The dimensions of the apparatus 1 can be any measure. The diameters of the in-flow end 11, out-flow end 17, distal opening 19 and proximal opening 16 are preferably within the range of and complimentary to the standard plumbing sizes and fitments for appliances. For example, plumbing lines in the home are often ¼ inch or ⅜ inch with international and domestic industry standards for threading and other measures. In at least one embodiment of the present invention, the in-flow nipple 12 and out-flow nipple 18 accommodates a variety of tubes by narrowing gradually from ⅜ inch to ¼ inch so a snug seal can be achieved regardless of the diameter of an inserted tube.

To sanitize the interior plumbing lines of an appliance using the present invention, the user begins by first turning off the water source in the environment which leads to the water line 21. For example, the water line 21 may be in the kitchen of a residential home and is located near an area for a refrigerator. Next the user places a bucket in front of the appliance for the collection of excess or spilled water. She also places a bucket in back of the appliance for the collection of excess or spilled water.

The user then continues by disconnecting the appliance plumbing line 23 from the water line 21. For example, the user disconnects the appliance plumbing line 23 that exits the back of the refrigerator from the water line 21 from the kitchen wall.

If a tighter seal is desired, the user optionally places a proximal end cap seal 31 onto the water line 21 in the environment and a distal end cap seal 32 onto the appliance plumbing line 23.

The user then continues by inserting the water line 21 through the first pinhole aperture 40 in the in-flow boot 20 and into the in-flow nipple 12 of the apparatus 1. She next inserts the appliance plumbing line 23 through the second pinhole aperture 40*b* in the out-flow boot 22 and into the out-flow nipple 18 of the apparatus 1. In order to make a more water tight connection, the user may push the proximal end cap seal 31 until it is engaged and flush with the in-flow boot 20. She optionally repeats this measure by pushing the distal end cap seal 32 until it is engaged and flush with the out-flow boot 22 to create a water tight seal.

Next, the user turns on the water source in the environment which leads to the water line 21, and allows the water to run through the apparatus for about 30 seconds. This allows the apparatus 1 and interior appliance plumbing lines 23 to fill with water. The user then turns off the water source for about 15 minutes, thereby allowing the sanitizing agent 29 inside the apparatus 1 to dissolve completely into solution.

Once dissolved, the user turns on the water source and allows approximately 5 to 7 gallons of water to flow through the apparatus 1, the interior appliance plumbing lines 23 of the appliance, and exit from the appliance. While the water flows during the sanitizing process, the user collects and discards the exiting water from the appliance using the available buckets as needed.

Once the sanitizing process is complete, the user turns off the water source in the environment, and removes the apparatus 1 from the water line 21 and appliance plumbing line 23. The user then reconnects the appliance plumbing line 23 to the water line 21 and turns on the water source leading to the water line 21 in the environment. Finally, the user allows water to run through the interior appliance plumbing lines 23 and exit from the appliance prior to regular use.

In an alternate embodiment of the present invention, the user can test the chlorine level of the water with a chlorine strip prior to beginning the sanitizing process to establish a baseline chlorine level. Once complete, the user may subsequently test the chlorine level of the water with a chlorine strip to compare chlorine level of the water to the baseline chlorine level. The user would continue to flush water through the appliance and repeatedly testing until the chlorine level in the appliance plumbing line 23 returns to baseline level.

In an alternate embodiment of the apparatus, the cartridge has a clear window to allow the user to observe the presence of the dye and completion of the dissolution of the sanitizing agent.

In an alternate embodiment of the invention, either or all of the hull 5, in-flow end 11, and out-flow end 17 can be made of a transparent material.

In an alternate embodiment of the present invention, either or all of the first sieve 24, second sieve 26 or third sieve 30 are made of paper.

The previously described versions of the present invention have many advantages, including and without limitation, the properties of i) sanitizing internal plumbing lines of appliances such as refrigerators with integrated ice makers and drinking water dispensers, ii) easily adaptable, iii) being able to be made in different sizes for use with various appliances, iv) optionally housing a variety of sanitizing agents, v) being used by an ordinary consumer, vi) 240 increasing safety and efficiency of internal plumbing line sanitation procedures, and vii) eliminating the need for expensive replacement of internal appliance plumbing lines. The device of the present invention is believed to accomplish all of the foregoing objectives. The invention does not require that all the advantageous features and all the advantages need to be incorporated into every embodiment of the invention.

Although the present invention has been described in considerable detail with reference to certain preferred versions thereof, other versions are possible. Therefore the spirit and scope of the appended claims should not be limited to the description of the preferred versions contained therein.

The reader's attention is directed to all papers and documents which are filed concurrently with this specification and which are open to public inspection with this specification, and the contents of all such papers and documents are incorporated herein by reference.

All the features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. As for "means for" elements, the applicant intends to encompass within the language any structure presently existing or developed in the future that performs the same function. The invention should therefore not be limited by the above described embodiment, method, and examples, but by all embodiments and methods within the scope and spirit of the invention.

What is claimed is:

1. An in-line internal plumbing line sanitizer for appliances apparatus which comprises:
    a) a cartridge having a proximal end, a distal end and formed by a rigid hull which is substantially cylinder shaped and having a first end and a second end, as well as an outer surface and inner surface, thereby defining a cylindrical void within;
    b) an in-flow end attached to the first end of the hull, said in-flow end having a substantially conical shape with an in-flow nipple extending from the in-flow end, said in-flow end and attached in-flow nipple and having an outer surface and an inner surface, thereby defining a conical void within, said in-flow nipple having a proximal opening at the proximal end of the apparatus;
    c) an out-flow end attached to the second end of the hull, said out-flow end having a substantially conical shape with an out-flow nipple extending from the out-flow end, said out-flow end and attached out-flow nipple having an second outer surface and a second inner surface thereby defining a second conical void within, said out-flow nipple having a distal opening at the distal end of the apparatus;
    d) an in-flow boot, which is generally cylindrical, over and covering the proximal opening of the in-flow nipple, said in-flow boot is a flexible material, and having a first pinhole aperture located in the end of the in-flow boot for receipt of an inserted water line from the environment into the in-flow nipple of the apparatus;
e) an out-flow boot, which is generally cylindrical, over an covering the distal opening of the out-flow nipple, said out-flow boot is a flexible material, and having a pinhole aperture located in the end of the out-flow boot for receipt of an inserted appliance plumbing line from the environment into the out-flow nipple of the apparatus;
f) a first sieve which is generally planar and having a circular perimeter located at the first end of and within the interior cylindrical void of the hull, said circular perimeter of the first sieve being affixed and forming a tight seam with the hull, said first sieve is a semi-permeable mesh having a plurality of perforations which allows the passage of fluid there through;
g) a second sieve which is generally planar and having a second circular perimeter located between the first sieve and the second end of the hull and within the interior cylindrical void of the hull, said second circular perimeter of the second sieve being affixed and forming a tight seam with the hull, said second sieve is a semi-permeable mesh having a plurality of perforations which allows the passage of fluid there through;
h) a sanitizing agent holding chamber in the interior cylindrical void of the hull near to the proximal end of the apparatus and defined by the void created by the interior surface of the hull, the first sieve and second sieve;
i) a mixing chamber in the interior void of the hull near to the distal end of the apparatus and defined by the void created by the inner surface of the hull, the second sieve and the out-flow end of the apparatus; and
j) a sanitizing agent in the sanitizing agent holding chamber, said sanitizing agent is a plurality of water soluble crystals or beads.

2. The apparatus as in claim 1 further comprising a third sieve which is generally planar and having a circular perimeter located between the second sieve and the second end of the hull, said circular perimeter of the first sieve being affixed and forming a tight seam with the hull, said third sieve is a semi-permeable mesh having a plurality of perforations which allows the passage of fluid there through.

3. The apparatus as in claim 2 where the third sieve is paper.

4. The apparatus as in claim 1 further comprising a proximal end cap seal inserted onto the water line in the environment,
said proximal end cap seal is a compressible material, and creates a tight seal between the water line and in-flow boot when adjoined.

5. The apparatus as in claim 1 further comprising a distal end cap seal inserted onto the appliance plumbing line in the environment,
said distal end cap seal is a compressible material, and creates a tight seal between the appliance plumbing line and out-flow boot when adjoined.

6. The apparatus as in claim 1 where the sanitizing agent is chlorine-based.

7. The apparatus as in claim 1 where the sanitizing agent further comprises a visible water soluble dye.

8. The apparatus as in claim 7 where the cartridge has a transparent window to allow the user to observe the visible water soluble dye in solution.

9. The apparatus as in claim 1 where the cartridge has a transparent window to allow the user to observe the completion of the dissolution of the sanitizing agent.

10. The apparatus as in claim 1 where the first sieve is paper.

11. The apparatus as in claim 1 where the second sieve is paper.

12. A method of sanitizing internal appliance plumbing lines using the apparatus of claim 1 which comprises:
a) turning off the water source in the environment which leads to the water line;
b) placing a bucket in front of the appliance for the collection of excess or spilled water;
c) placing a bucket in back of the appliance for the collection of excess or spilled water;
d) disconnecting the appliance plumbing line from the water line;
e) placing proximal end cap seal onto the water line in the environment;
f) placing distal end cap seal onto the appliance plumbing line;
g) inserting the water line through the first pinhole aperture in the in-flow boot and into the in-flow nipple of the apparatus;
h) inserting the appliance plumbing line through the aperture in the out-flow boot and into the out-flow nipple of the apparatus;
i) pushing the proximal end cap seal until it is engaged and flush with the in-flow boot, thereby creating a seal;
j) pushing the distal end cap seal until it is engaged and flush with the out-flow boot, thereby creating a seal;
k) turning on the water source in the environment which leads to the water line;
l) allowing the water to run through the apparatus for about 30 seconds to allow the apparatus and interior appliance plumbing lines to fill with water;
m) turning off the water source for about 15 minutes, thereby allowing the sanitizing agent inside the apparatus to dissolve completely;
n) turning on the water source and allowing approximately 5 to 7 gallons of water to flow through the apparatus, the interior plumbing lines of the appliance, and exit from the appliance;
o) collecting the exiting water from the appliance in the available buckets as needed;
p) turning off the water source in the environment;
q) removing the apparatus from the water line and appliance plumbing line;
r) reconnecting the appliance plumbing line to the water line;
s) turning on the water source leading to the water line in the environment; and
t) allowing water to run through the interior appliance plumbing lines and exit from the appliance prior to regular use.

13. The method as in claim 12 further comprising testing the chlorine level of the water with a chlorine strip prior to beginning the method to establish a baseline chlorine level.

14. The method as in claim 8 further comprising testing the chlorine level of the water with a chlorine strip after completing the method to compare chlorine level of the water to the baseline chlorine level.

15. The method as in claim 9 further comprising flushing water through the appliance and testing with chlorine strips until the chlorine level returns to baseline level.

* * * * *